(12) United States Patent
Watanabe et al.

(10) Patent No.: US 7,005,048 B1
(45) Date of Patent: Feb. 28, 2006

(54) GLUCOSE SENSOR

(75) Inventors: Motokazu Watanabe, Katano (JP);
Keiko Yugawa, Nara (JP); Toshihiko Yoshioka, Hirakata (JP); Shiro Nankai, Hirakata (JP); Junko Nakayama, Ehime (JP); Shoji Miyazaki, Matsuyama (JP); Hideyuki Baba, Matsuyama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/807,692

(22) PCT Filed: Oct. 2, 2000

(86) PCT No.: PCT/JP00/06853

§ 371 (c)(1),
(2), (4) Date: Apr. 17, 2001

(87) PCT Pub. No.: WO01/25776

PCT Pub. Date: Apr. 12, 2001

(30) Foreign Application Priority Data

Oct. 5, 1999 (JP) .................................. 11-284871

(51) Int. Cl.
*G01N 27/327* (2006.01)
(52) U.S. Cl. .............................. 204/403.04; 204/403.14
(58) Field of Classification Search ............... 204/403, 204/403.14, 403.09, 403.1, 403.04, 403.11
See application file for complete search history.

(56) References Cited

U.S. PATENT DOCUMENTS

| 4,098,972 | A | 7/1978 | Ogawa et al. |
|---|---|---|---|
| 4,545,382 | A | 10/1985 | Higgins et al. |
| 4,711,245 | A | 12/1987 | Higgins et al. |
| 5,334,508 | A | 8/1994 | Hoenes |
| 5,378,628 | A | 1/1995 | Gratzel et al. |
| 5,424,204 | A | 6/1995 | Aoyama et al. |
| 5,466,575 | A | 11/1995 | Cozzette et al. |
| 5,554,339 | A | 9/1996 | Cozzette et al. |
| 5,682,884 | A | 11/1997 | Hill et al. |
| 5,762,770 | A | 6/1998 | Pritchard et al. |
| 5,804,047 | A | 9/1998 | Karube et al. |
| 5,820,551 | A | 10/1998 | Hill et al. |
| 5,897,995 | A | 4/1999 | Vroemen et al. |
| 5,942,424 | A * | 8/1999 | Woodward et al. ......... 435/168 |
| 5,997,817 | A | 12/1999 | Crismore et al. |

(Continued)

FOREIGN PATENT DOCUMENTS

EP 0078636 5/1983

(Continued)

OTHER PUBLICATIONS

CAPLUS abstract of Howaldt et al. ("A continuous enzyme membrane reactor retaining the native nicotinamide cofactor NAD(H)", Ann. N. Y. Acad. Sci. (1990), 5899Biochem. Eng. 6), 253-60).*

(Continued)

*Primary Examiner*—Alex Noguerola
(74) *Attorney, Agent, or Firm*—McDermott Will & Emery LLP (57) ABSTRACT

The present invention provides a high-performance glucose sensor having excellent storage stability and an improved response characteristic. This sensor comprises: an electrically insulating base plate; an electrode system including at least a working electrode and a counter electrode formed on the base plate; and a reaction layer containing at least pyrrolo-quinoline quinone dependent glucose dehydrogenase, formed in contact with or in the vicinity of the electrode system, and the reaction layer contains at least one kind of additive selected from the group consisting of gluconic acid and salts thereof.

13 Claims, 7 Drawing Sheets

U.S. PATENT DOCUMENTS

| | | | |
|---|---|---|---|
| 6,025,203 | A | 2/2000 | Vetter et al. |
| 6,059,946 | A | 5/2000 | Yukawa et al. |
| 6,071,391 | A | 6/2000 | Gotoh et al. |
| 6,077,660 | A | 6/2000 | Wong et al. |
| 6,218,134 | B1 * | 4/2001 | Yamauchi et al. ............ 435/7.9 |
| 6,270,637 | B1 | 8/2001 | Crismore et al. |
| 6,773,564 | B1 * | 8/2004 | Yugawa et al. ........ 204/403.14 |

FOREIGN PATENT DOCUMENTS

| | | | |
|---|---|---|---|
| EP | 0 125 137 | | 11/1984 |
| EP | 0 357 027 | A2 | 3/1990 |
| EP | 0 502 504 | A1 | 9/1992 |
| EP | 0 636 879 | A2 | 2/1995 |
| EP | 0 735 363 | A1 | 10/1996 |
| EP | 0 744 466 | A2 | 11/1996 |
| EP | 0 872 728 | A1 | 10/1998 |
| EP | 0 992 589 | A2 | 4/2000 |
| JP | 2-62952 | | 3/1990 |
| JP | 09-262086 | A * | 10/1991 |
| JP | 9-140378 | | 6/1997 |
| JP | 10-227755 | | 8/1998 |
| JP | 10-227755 | A * | 8/1998 |
| JP | 11-243949 | | 9/1999 |
| WO | WO 98 35225 | | 8/1998 |

OTHER PUBLICATIONS

English language translation of Yoshioka et al. (JP 10-227755).*
English language translation of Akio et al. (JP 09-262086).*
CAPLUS abstract of Kurtinaitiens et al. ("Mediated glucoes biosensor based on PQQ-dependent glucose dehydrongenase," Biologija (1995), (1-2), 50-2).*
Wilson, et al. "Review Article:Glucose Oxidase: an Ideal Enzyme" Biosensors & Bioelectronics 7 (1992) 165-166.
Matsushita, et al. "Bacterial Quinoproteins Glucose Dehydrogenase and Alcohol Dehydrogenase" Principles and Applications of Quinoproteins, ed. Victor L. Davidson (1992) 47-63.
Shul'ga, et al. "The Effect of Divalent Metal Ions on the Performance of a Glucose-Sensitive ENFET Using Potassium Ferricyanide as an Oxidising Substrate" Sensors and Actuators B 26-27 (1995) 432-435.
CAPLUS Kawaguri, et al. "Biosensor for Microanalysis of Body Fluids." JP 02102448 A2.
JAPIO Mariko, et al. "Biosenso." JP 02102448 A.
"2,4,6-Collidine" Encyclopedia of Reagents for Organic Synthesis.
"Colicins"and "Bacteriocins" Encyclopedia of Molecular Biology and Molecular Medicine.
Goodwin, et al. "The Biochemistry, Physiology and Genetics of PQQ and PQQ-containing Enzymes" Advances in Microbial Physiology vol. 40, ed. R.K. Poole (1998) 1-80.
Yoshioka, et al. "Disposable Biosensor Based on Bioelectrochemistry" National Technical Report vol. 42 No. 2 (Apr. 1996) 71-75.
CAPLUS Cucinotta, et al. "Three-Dimensional Cyclodextrin: a New Class of Hosts by Trehalose Capping of beta.-cyclodextrin." J. Inclusion Phenom. Mol. Recognit. Chem. (1996) 25(1-3, 39-42).
CAPLUS Takahashi, et al. "Effect of a Trehalase Inhibitor, Validoxylamine A, on Three Species of Flies" Appl. Entomol. Zool. (1995), 30(1, 231-239).
Yoshida, et al. "Thr424 to Asn Substitution Alters Bivalent Metal Specificity of Pyrroloquinoline Quinone Glucose Dehydrogenase" 1997, J. Biochem. Mol. Biol. & Biophys., vol. 1, pp. 89-93.
Witaro, et al. "Secondary Structure Study of Pyrroloquinoline Quinone Glucose Dehydrogenase" 1999, J. Biochem. Mol. Biol. & Biophys., vol. 1, pp. 209-213.
Sode, et al. "Glu742 Substitution To Lys Enhances The EDTA Tolerance of *Escherichia Coli* PQQ Glucose Dehydrogenase" 1994, Biotechnology Letters, vol. 16, No. 5, pp. 455-460.
Witaro, et al. "Site-Directed Mutagenesis Study on the Thermal Stability of a Chimeric PQQ Glucose Dehydrogenase and Its Structural Interpretation" 1999, Applied Biochemistry and Biotechnology, vol. 77-79, pp. 159-168.
Laurinavicius, et al. "Oxygen Insensitive Glucose Biosensor Based on PQQ-Dependent Glucose Dehydrogenase" 1999, Analytical Letters, vol. 32(2), pp. 299-316.
Matsushita, et al. "Soluble and Membrane-bound Quinoprotein D-Glucose Dehydrogenases of the *Acinetobacter calcoaceticus*: The Binding Process of PQQ to the Apoenzymes" 1995, Biosci. Biotech. Biochem, vol. 59(8), pp. 1548-1555.
Matsushita, et al. "Membrane-bound D-Glucose Dehydrogenase from *Pseudomonas* sp. : Solubilization, purification and Characterization" 1980, Agric. Biol. Chem. vol. 44(7), pp. 1505-1512.
Ameyama, et al. "Purification and Characterization of the Quinoprotein D-Glucose Dehydrogenase Apoenzyme from *Escherichia coli*" De1986, Agric. Biol. Chem., vol. 50(1), pp. 49-57.
Ameyama, et al. "D-Glucose Dehydrogenase of Gluconobacter suboxydans: Soubilization, Purification and Characterization" 1981, Agric. Biol. Chem., vol. 45(4), pp. 851-861.
Hauge, Jens G. "Glucose Dehydrogenase of *Bacterium anitratum*: an Enzyme with a Novel Prosthetic Group" 1964, vol. 239, No. 11, pp. 3630-3639.
Sode, et al. "Subzero Temperature Operating Biosensor Utilizing an Organic Solvent and Quinoprotein Glucose Dehydrogenase" 1993, Biotechnology and Bioengineering, vol. 42, pp. 251-254.
Ikeda,, et al. "Electrochemical Monitoring of In Vivo Reconstitution of Glucose Dehydrogenase in *Escherichia coli* Cells With Externally Added Pyrroloquinoline Quinone" 1998, Journal of Electroanalytical Chemistry, vol. 449, pp. 219-224.
D'Costa, et al. "Quinoprotein Glucose Dehydrogenase and its Application in an Amperometric Glucose Sensor" 1986, Biosensors, vol. 2, pp. 71-87.
Dewanti, et al. "$Ca^{2+}$ -Assisted, Direct Hydride Transfer, and Rate-Determining Tautomerization of C5-Reduced PQQ to $PQQH_2$, in the Oxidation of β-D-Glucose by Soluble, Quinoprotein Glucose Dehydrogenase" 2000, Biochemistry 2000 vol. 39 pp. 9384-9392.
Sode, et al. "Construction and Characterization of a Chimeric *Escherichia coli* PQQ Glucose Dehydrogenase (PQQGHD) with Increased EDTA Tolerance", 1997, Denki Kagaku, vol. 65, No. 6, pp. 444-451.
Yamazaki, et al. "Increased Thermal Stability of Glucose Dehydrogenase by Cross-Linking Chemical Modification" 1999, Biotechnology Letters, vol. 21, pp. 199-202.
Sode, at al. "Construction and Characterization of A Linked-Dimeric Pyrroloquinoline Quinone Glucose Dehydrogenase" 1999, Biotechnology Letters, vol. 21, pp. 707-710.
Sode, et al. "Stablization of Pyrroloquiolline quinone Glucose Dehydrogease By Cross-Linking Chemical Modification" 1996, Biotechnology Letters, vol. 18, No. 9, pp. 997-1002.

Sode, et al. "Preparation of Lyophilized Pyrroloquinoline Quinone Glucose Dehydrogenase Using Trehalose As An Additive" 1997, Biotechnology Techniques, vol. 11, No. 8, pp. 577-580.

Sode, at al. "Over Expression of PQQ Glucose Dehydrogenase in *Echerichia coli* Under Holo Enzyme Forming Condition" 1994, vol. 16, No. 12, pp. 1265-1268.

Sode, at al. "Elucidation of The Region Responsible For Edta Tolerance In PQQ Gluccose Dehydrogenases By Construction *Escherichia coli* and Acinetobacter Calcoaceticus Chimeric Enzymes" 1995, Biochemical and Biophysical Research Communications, vol. 211, No. 1, pp. 268-273.

Sode, et al. "A Novel Thermostable Glucose Dehydrogenase Varying Temperature Properties By Altering Its Quaternary Structures" 1996, Enzyme and Microbial Technology, vol. 19, pp. 82-85.

Sode, at al. "Thermostable Chimeric PQQ Glucose Dehydrogenase" 1995, Federation of European Biochemical Societies Letters, vol. 364, pp. 325-327.

Sode, at al. "Increased Production of Recombinant Pyrroloquinoline Quinone (PQQ) Glucose Dehydrogenase By Metabolically Engineered *Escherichia coli* Strain Capable of PQQ Biosynthesis" 1996, Journal of Biotechnology, pp. 239-243.

Sode, at al. "Effect of PQQ Glucose Dehydrogenase Overexpression In *Escherichia coli* On Sugar-Dependent Respiration" 1995, Journal of Biotechnology, vol. 43, pp. 41-44.

Olsthoorn, et al. "Negative Cooperativity In The Steady-State Kinetics of Sugar Oxidation By Soluble Quinoprotein Glucose Dehydrogenase From Acinetobacter Calcoaceticus" 1998, Eur. J. Biochem, pp. 255-261.

Martin, et al. "High Current Density "Wired" Quinoprotein Glucose Dehydrogenase Electrode" 1993, Analytical Chemistry, vol. 65, No. 3, pp. 238-241.

Yoshida, et al. "Engineering a Chimeric Pyrroloquinoline Quinone Glucose Dehydrogenase: improvement of EDTA tolerance, thermal stability and substrate specificity" 1999, Protein Engineering, vol. 12, No. 1, pp. 63-70.

Sode, et al. "Improved Substrate Specificity and Dynamic Range For Glucose Measurement of *Escherichia coli* PQQ Glucose Dehydrogenase By Site Directed Mutagenesis" 1997, Biotechnology Letters, vol. 19, No. 11, pp. 1073-1077.

Yamazaki, et al. "Subunit Analyses of a Novel Thermostable Glucose Dehydrogenase Showing Deifferent Temperature Properties According to Its Quaternary Structure" 1999 Applied Biochemistry and Biotechnology, vol. 77-79, pp. 325-335.

Dokter, et al. "Cytochrome b-562 from Acinetobacter Calcoaceticus L.M.D. 79.41" Biochem J., vol. 254, pp. 131-138.

Sode, et al., "Isolation of a Marine Bacterial Pyrroloquinoline Quinone-Dependent Glucose Dehydrogenase" 1995, J. Mar. Biotechnol, vol. 2, pp. 214-218.

Geerlof, et al. "Haem-Containing Protein Complexes of Acinetobacter Calcoaceticus As Secondary Electron Acceptors for Quinoprotein Glucose Dehydrogenase" 1989, Antonie van Leeuwenhoek, vol. 56, pp. 81-84.

Jin, et al. "PQQ as Redox Shuttle for Quinoprotein Glucose Dehydrogenase" 1998, Biol. Chem., vol. 379, pp. 1207-1211.

Hauge, Jens G. "Kinetics and Specificity of Glucose Dehydrogenase From Bacterium Anitraturn" 1960, Biochim. biophys. Acta, vol. 45, pp. 263-269.

Oubrie, et al. "The 1.7 A Crystal Structure of the Apo Form of the Soluble Quinoprotein Glucose Dehydrogenase from *Acinetobacter calcoacetus* Reveals a Novel Internal Conserve Sequence Repeat" 1999, vol. 289, pp. 319-333.

Hauge, Jens G. "Purification and Properties of Glucose Dehydrogenase and Cytochrome b from Bacterium Anitratum" 1960, Biochim. Biophys. Acta, vol. 45, pp. 250-262.

Wanner, et al. "First Experimental Structure of a 1:1 Metal Complex with a PPQ Cofactor Derivative Ouside Dehydrogenase Enzymes" 1999, Inorganic Chemistry, vol. 38, No. 11, pp. 2753-2755.

Dewanti, et al. "Reconstitution of Membrane -Integrated Quinoprotein Glucose Dehydrogenase Apoenzyme with PQQ and the Holoenzyme's Mechanism of Action" 1998, Biochemistry, vol. 37, No. 19, pp. 6810-6818.

Alkasrawi, et al. "A Redox Hydrogel Integrated PQQ-Glucose Dehydrogenase Based Glucose Electrode" 1999, Anal. Communication, vol. 36, pp. 395-398.

Mor, et al. "Assay of Glucose Using an Electrochemical Enzymatic Sensor" 1977, Analytical Biochemistry, vol. 79, pp. 319-328.

Duine, et al. "Glucose Dehydrogenase From Acinetobacter Calcoaceticus" FEBS Letters, 1979, vol. 108, No. 2, pp. 443-446.

Iswantini, et al. "Electrochemical Measurements of Glucose Dehydrogenase Activity Exhibited By *Escherichia coli* Cells; Effects of the Additions of Pyrroloquinoline Quinone, Magnesium or Calcium Ions and Ethylenediaminetetraacetic Acid" 1998, Bioelectrochemistry and Bioenergetics, vol. 46, pp. 249-254.

Matsushita, et al. "Quinoprotein D-glucose Dehydrogenases in Acinetobacter Calcoaceticus LMD 79:41: Purification and Characterization of the Membrane-Bound Enzyme Distinct from the Soluble Enzyme" 1989, Antonie van Leeuwenhoek, vol. 56, pp. 63-72.

Cozier, et al. "Structure of the Quinoprotein Glucose Dehydrogenase of *Escherichia coli* Modelled on that of Methanol Dehydrogenase from Methylobacterium Extorquens" 1995, Biochem. J., vol. 312, pp. 679-685.

Sode, et al. "Preparation of Lyophilized Pyrroloquinoline Quinone Glucose Dehydrogenase Using Trehalose as an Additive" 1997 Biotechnology Techniques vol. 11, No. 8, pp. 577-580.

"Glucose Oxidase" Toyobo Enzymes (1998).

* cited by examiner

GLUCOSE SENSOR

This application is the national stage under 35 U.S.C. 371 of PCT/JP00/06853, filed on Oct. 2, 2000.

TECHNICAL FIELD

The present invention relates to a glucose sensor capable of rapidly and simply quantifying a specific component in a sample with high accuracy. More specifically, the present invention relates to a glucose sensor using pyrrolo-quinoline quinone dependent glucose dehydrogenase.

BACKGROUND ART

Conventionally, a variety of biosensors have been proposed as a system for simply quantifying a specific component in a sample solution without diluting or stirring the sample solution. As one example of the biosensors, for instance, the following sensor has been known (Japanese Laid-Open Patent Publication No. Hei 2-062952).

This biosensor is fabricated by forming an electrode system comprising a working electrode, a counter electrode and a reference electrode on an electrically insulating base plate by screen printing or other method and forming thereon an enzyme reaction layer comprising a hydrophilic polymer, an oxidoreductase and an electron acceptor in contact with the electrode system.

When a sample solution containing a substrate is dropped on the enzyme reaction layer of this biosensor, the enzyme reaction layer is dissolved, and the substrate and the enzyme react with each other, thereby reducing the electron acceptor. Thereafter, the reduced electron acceptor is electrochemically oxidized, and the concentration of the substrate in the sample solution can be determined from an oxidation current value obtained in this oxidation.

According to the biosensor as mentioned above, in theory, it is possible to measure various substances by selecting an enzyme whose substrate is a substance to be measured.

For instance, if glucose oxidase is selected as the enzyme, it is possible to fabricate a glucose sensor for measuring the concentration of glucose in a sample solution.

In the biosensor having the structure as mentioned above, the enzyme is normally retained in the sensor in a dried state. Since the enzyme is composed mainly of protein, if the enzyme is exposed to moisture in the air, etc. over a long period, there is a risk of the denaturation of the enzyme. Moreover, in an extreme case, there is a risk of the inactivation of the enzyme.

For this reason, if the sensor is stored for a long time, the enzyme activity is lowered and the amount of enzyme that reacts with the substrate becomes insufficient, and thus there is a possibility that the resultant response current value is not proportional to the concentration of the substrate.

Therefore, in order to obtain a biosensor excelling in the storage stability, it is important to provide an environment for retaining the activity of the enzyme for a long time in the vicinity of the enzyme. Moreover, it is necessary to improve the response of the sensor by facilitating smooth movement of the electrons and substrate during an enzyme reaction.

On the other hand, in order to fabricate a high-performance glucose sensor, pyrrolo-quinoline quinone dependent glucose dehydrogenase (hereinafter referred to as the "PQQ-GDH") is used as the enzyme. In the glucose sensor using the PQQ-GDH, since oxygen is not involved in the catalytic reaction of the PQQ-GDH, this sensor has a characteristic that the enzyme reaction does not receive any effect of dissolved oxygen in blood, etc. Therefore, the measurement value given by this glucose sensor never varies depending on the oxygen partial pressure in the sample solution. In other words, it is possible to obtain a high-performance sensor.

However, in the case where the PQQ-GDH is used as the enzyme of the glucose sensor, it has been revealed that there is a problem that the response value is lowered by storage. This means that the response value is lowered as the period of storage of the glucose sensor is longer. It is impossible to always use the sensor at a certain time after the fabrication of the sensor. Hence, with a sensor whose response value will be lowered by storage, it is impossible to accurately quantify the concentration of glucose.

In view of such problems, it is an object of the present invention to provide a high-performance glucose sensor having excellent storage stability and an improved response characteristic in an initial stage.

DISCLOSURE OF INVENTION

A glucose sensor according to the present invention is a glucose sensor comprising an electrically insulating base plate; an electrode system including at least a working electrode and a counter electrode formed on the base plate; and a reaction layer containing at least pyrrolo-quinoline quinone dependent glucose dehydrogenase, formed in contact with or in the vicinity of the electrode system, and is characterized in that the reaction layer contains at least one kind of additive selected from the group consisting of gluconic acid and salts of gluconic acid.

It is preferred that the reaction layer further contains at least one kind of additive selected from the group consisting of phthalic acid, salts of phthalic acid, maleic acid, salts of maleic acid, succinic acid and salts of succinic acid.

It is preferred that the reaction layer further contains calcium ions.

It is preferred that the salt of gluconic acid is potassium gluconate, sodium gluconate, calcium gluconate, cobalt gluconate, or copper gluconate.

It is preferred that the reaction layer further contains an electron mediator.

BEST MODE FOR CARRYING OUT THE INVENTION

As described above, a glucose sensor of the present invention is obtained by adding gluconic acid and/or a salt thereof to a reaction layer containing the PQQ-GDH as an enzyme.

The present inventors have found that the storage stability of the sensor can be significantly improved by adding gluconic acid and/or a salt thereof to the reaction layer containing the PQQ-GDH. It is deemed that gluconic acid and/or the salt thereof protects the PQQ-GDH from changes in the environment such as the conditions of temperature, humidity and charge, thereby improving the storage stability. In order to enhance such an effect, it is preferred to form the reaction layer by a method in which a mixed solution of gluconic acid and/or a salt thereof and the PQQ-GDH is dropped to a place where the reaction layer is to be formed and then dried. When the reaction layer is formed according to this method, since the enzyme is surrounded by gluconic acid at a molecular level, it is possible to effectively protect the PQQ-GDH from changes in the environment such as the conditions of temperature, humidity and charge. As a result, the activity of the enzyme can be stabilized for a long time.

The present inventors have further found that the response characteristic of the sensor before storage, i.e., the initial characteristic, is improved by adding gluconic acid and/or a salt thereof to the reaction layer containing the PQQ-GDH. Since gluconic acid or the salt thereof is easily dissolved in water, if it is contained in the reaction layer, when a sample solution is added to the reaction layer, the reaction layer is immediately dissolved in the sample solution, and thus the enzyme reaction and the electrode reaction can proceed smoothly, which is advantageous.

Examples of additives which are expected to produce these effects include potassium gluconate, sodium gluconate, calcium gluconate, cobalt gluconate and copper gluconate as well as gluconic acid. In particular, when potassium gluconate is used, it is possible to obtain a glucose sensor having excellent storage stability and response characteristic and a very low blank value. Here, the blank value is a sensor response value obtained by the use of a sample solution containing no glucose as a substrate, for example, water.

Although phthalic acid, maleic acid, succinic acid and the salts thereof are not as good as gluconic acid and salts of gluconic acid when used alone, since they have an effect of protecting the PQQ-GDH, if they are added together with gluconic acid or a slat thereof, it is possible to further improve the storage stability of the sensor by the synergistic effect. Besides, since phthalic acid, maleic acid, succinic acid and the salts thereof are easily dissolved in water, if they are contained in the reaction layer, when the sample solution is added to the reaction layer, the reaction layer is immediately dissolved in the sample solution and the enzyme reaction and electrode reaction can proceed smoothly, thereby improving the initial characteristic.

Phthalic acid, maleic acid, succinic acid and the salts thereof are all compounds that can be used as a buffer, and may be added to the reagent for forming the reaction layer by adjusting them to a predetermined pH with acid such as hydrochloric acid and acetic acid or alkali such as NaOH and KOH, if necessary. A suitable pH is between 5.0 and 8.5. Of course, compounds obtained by adding these additives to other buffer may be used.

Since gluconic acid, phthalic acid, maleic acid, succinic acid and the salts thereof are compounds that easily absorb moisture, they should be added during the fabrication of a glucose sensor so that they first come into contact with the enzyme during the fabrication of the glucose sensor, instead of adding them to the enzyme in advance. It is preferred that glucose sensors containing these additives are stored in a sealed state. When storing the glucose sensor, it is preferred to store it in a sealed container containing therein a moisture absorbent such as silica gel.

In a disposable type sensor for measuring 0.5 to 5 $\mu$l blood as a sample solution, for the amount of enzyme of 0.2 to 20 U/sensor, the amount of gluconic acid or a salt thereof should be within a range of 1.5 to 150 $\mu$g/sensor, and is preferably between 15 and 50 $\mu$g/sensor from the viewpoint of the storage stability and a reduction of the blank value. Meanwhile, for the above-mentioned sensor, the amount of phthalic acid, maleic acid, succinic acid and the salts thereof to be added is preferably between 0.025 and 25 $\mu$g/sensor, and more preferably between 0.1 and 3 $\mu$g/sensor. Here, U represents unit.

An example of other preferable additive is calcium chloride that gives calcium ions. In general, calcium ions are necessary when the PQQ-GDH forms a dimer. Therefore, when calcium ions are introduced into the reagent for forming the reaction layer by calcium chloride, etc., it is possible to prevent dissociation of the PQQ-GDH to a dimer during or after the fabrication of the sensor, and therefore the calcium ions are useful for retaining the activity of PQQ-GDH. The amount of calcium chloride to be added with respect to the above-mentioned sensor is preferably between 5 and 70 ng (nanogram)/sensor.

It is preferred that the reaction layer of the biosensor of the present invention contains an electron mediator which is reduced with the enzyme reaction. For this electron mediator, it is possible to use potassium ferricyanide, p-benzoquinone and derivatives thereof, phenazine methosulphate, methylene blue, ferrocene and derivatives thereof.

The reaction layer of the biosensor of the present invention may contain a hydrophilic polymer. By adding a hydrophilic polymer to the reaction layer, it is possible to prevent separation of the reaction layer from the electrode system surface or the base plate surface. Moreover, since the hydrophilic polymer has the effect of preventing cracks in the reaction layer surface, it is effective for an increase of the reliability of the biosensor.

As such a hydrophilic polymer, it is possible to suitably use carboxymethyl cellulose, hydroxyethyl cellulose, hydroxypropyl cellulose, methyl cellulose, ethyl cellulose, ethyl hydroxyethyl cellulose, carboxyethyl cellulose, polyvinyl pyrrolidone, polyvinyl alcohol, polyamino acid such as polylysine, polystyrene sulphonate, gelatin and derivatives thereof, polymers of acrylic acid and salts thereof, polymers of methacrylic acid and salts thereof, starch and derivatives thereof, polymers of maleic anhydride and salts thereof, agarose gel and derivatives thereof.

The reaction layer in the biosensor may be placed at various positions as well as on the electrode system formed on the electrically insulating base plate if it does not impair the effects of the present invention. For example, it is possible to place the reaction layer at a position other than on the electrode system of the base plate. Moreover, the biosensor preferably includes a cover member. This cover member is combined with the base plate to form a sample solution supply path between the cover member and the base plate, for supplying the sample solution to the electrode system. It is possible to position the reaction layer on this cover member's face exposed to the sample solution supply path.

As the method for measuring a current for oxidizing the electron mediator reduced with the enzyme reaction, there are two types of methods: a two-electrode method using only a working electrode and a counter electrode; and a three-electrode method further comprising a reference electrode, and the three-electrode method enables more accurate measurement.

Here, for the reaction layer of the biosensor of the present invention, in addition to the above-mentioned additives, it is possible to add other stabilizer unless it impairs the effects of the present invention. Examples of such a stabilizer include metallic salts, proteins, amino acids, sugars, organic acids, and surface active agents.

Examples of metallic salt include halides such as strontium and manganese, the sulfates and nitrites thereof. Preferred proteins are ones that do not affect the enzyme activity, and examples of such proteins include bovine serum albumin (BSA), egg albumin, and gelatin.

As the amino acid, it is possible to use glycylglycine, polylysine, etc. as well as typical amino acids such as lysine, histidine and glutamic acid. Among them, highly water-soluble amino acids are preferable.

As the sugar, it is possible to use any kinds of sugars, such as monosaccharide, disaccharide, oligosaccharide and polysaccharide. It is also possible to use their derivatives. More specifically, examples of sugars include glucose, fructose, galactose, mannose, xylose, sucrose, lactose, maltose, trehalose, maltotriose, maltocylcyclodextrin, α-cyclodextrin, β-cyclodextrin, γ-cyclodextrin, dextrin, amylose, glycogen, starch, inulin, glucosamine, inositol, mannitol, sorbitol, ribitol and deoxyglucose.

Examples of the organic acid include α-ketoglutaric acid, malic acid, fumaric acid, cholic acid, and deoxycholic acid.

As the surface active agent, it is preferred to use a nonionic surface active agent.

In addition, boric acid, borax, potassium chloride, sodium chloride, ammonium sulfate, glycerol, Ficoll, EDTA, EGTA, DTT, DTE, GSH, 2-mercaptoethanol, etc. may be added.

The amount of these stabilizers to be added is preferably between 0.01 and 100 parts by weight based on 100 parts by weight of the PQQ-GDH.

In order to prevent pyrrolo-quinoline quinone (PQQ) as a coenzyme from being separated from the PQQ-GDH, PQQ may be added to the reaction layer. The amount of PQQ to be added is preferably between 0.04 and 20 ng/sensor.

As the enzyme PQQ-GDH for use in the present invention, it is possible to use PQQ-GDH from any source.

The glucose sensor using the PQQ-GDH of the present invention that contains the above-mentioned additives and further contains the above-mentioned stabilizers, if necessary, can retain its performance at low costs without viciously affecting the basic performance of the enzyme.

Some examples will be used to explain the present invention, but the present invention is not necessarily limited to only these examples.

Figure 1:
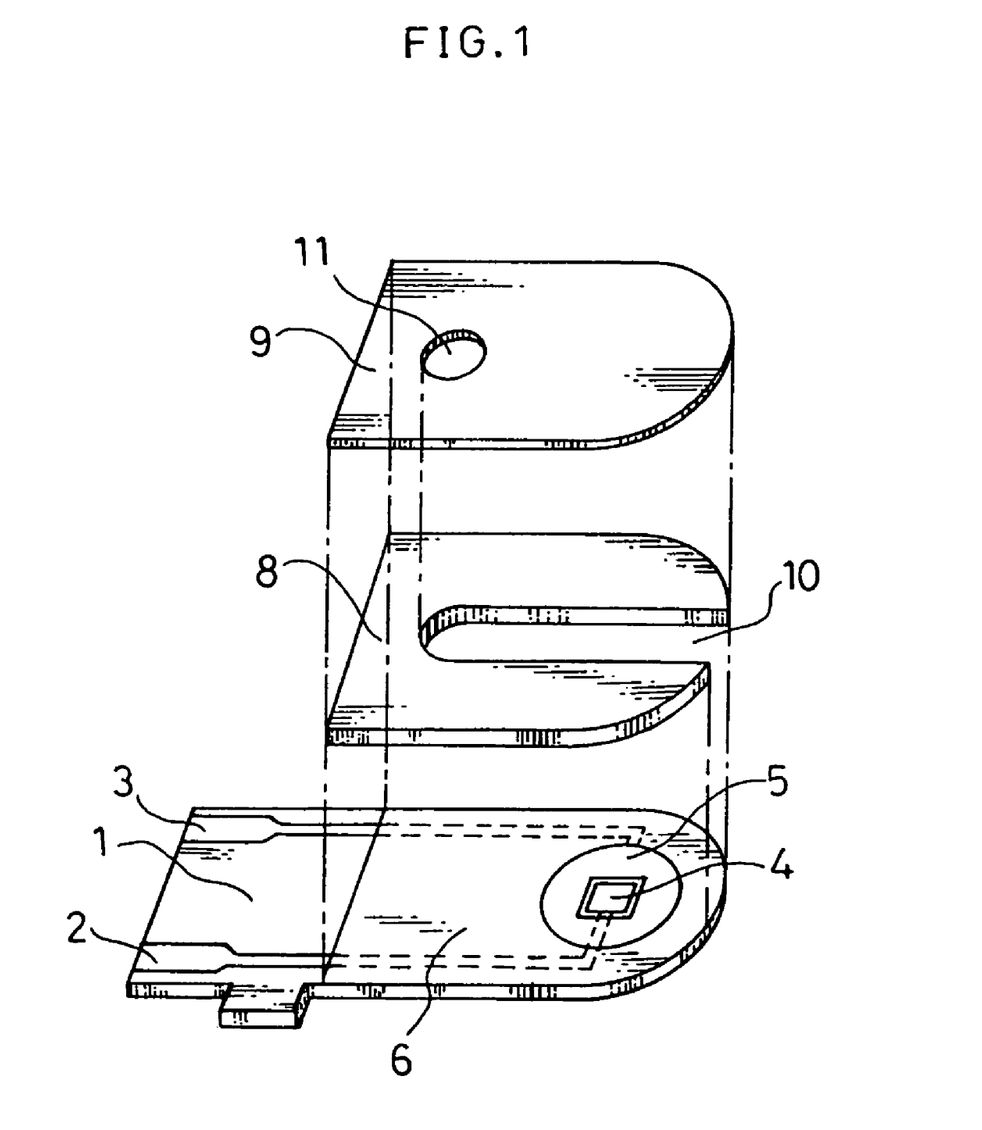
FIG. 1 is a perspective view of a glucose sensor according to one example of the present invention, omitting a reaction layer.

FIG. 1 is an exploded perspective view of a biosensor according to one example of the present invention, omitting the reaction layer. A silver paste is printed on an electrically insulating base plate 1 made of polyethylene terephthalate by screen printing to form leads 2 and 3. Subsequently, a conductive carbon paste containing a resin binder is printed on the base plate 1 to form a working electrode 4. This working electrode 4 is in contact with the lead 2. Further, an insulating paste is printed on the base plate 1 to form an insulating layer 6. The insulating layer 6 covers the peripheral portion of the working electrode 4, so that the area of the exposed portion of the working electrode 4 is kept constant. Next, a ring-shaped counter electrode 5 is formed by printing a conductive carbon paste containing a resin binder on the base plate 1 so as to be in contact with the lead 3.

After forming a reaction layer on the insulating base plate 1 in a later-described manner, a spacer 8 including a slit 10 and a cover 9 having an air bent 11 are adhered to each other in a positional relationship as shown by the dashed lines of FIG. 1, thereby fabricating the biosensor. A sample solution supply path is formed in the portion of the slit 10 of the spacer 8. The open end of the slit 10 at an end portion of the sensor serves as the sample supply port to the sample solution supply path.

Figure 2:
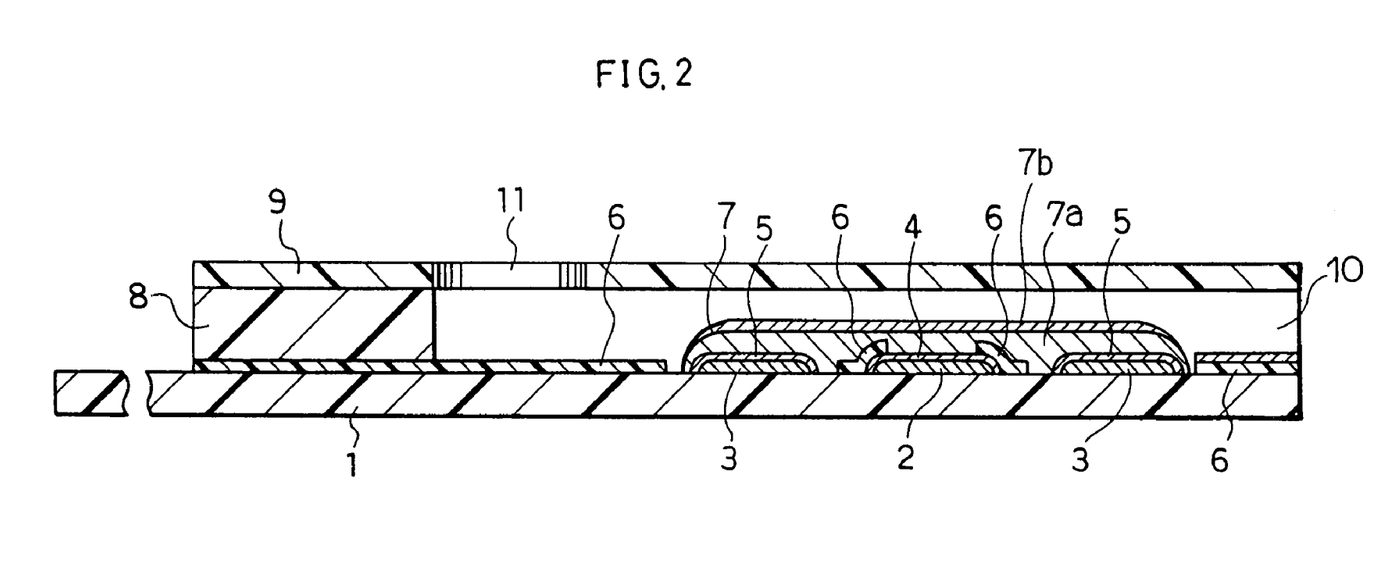
FIG. 2 is a vertical cross-sectional view of the vital part of the glucose sensor shown in FIG. 1.

FIG. 2 is a vertical cross sectional view of the biosensor of the present invention. A reaction layer 7 containing an enzyme and an electron mediator is formed on the base plate 1 on which the electrode system is formed. The reaction layer 7 is preferably formed on the electrode system, but it may be formed in the vicinity of the electrode system, for example, on the cover side so that it is exposed to the sample solution supply path. In the illustrated example, the reaction layer 7 is composed of a hydrophilic polymer layer 7a and a layer 7b which contains the PQQ-GDH and additives and is formed on the hydrophilic polymer layer 7a.

COMPARATIVE EXAMPLE 1

5 μl of a 0.5 wt % aqueous solution of sodium salt of carboxymethyl cellulose (hereinafter abbreviated to "CMC") as a hydrophilic polymer was dropped onto the electrode system of the base plate 1 of FIG. 1 and dried in a 50° C. hot-air drier for 10 minutes to form a CMC layer 7a. Subsequently, 5 μl of a mixed aqueous solution containing 1000 U/ml of PQQ-GDH and 50 mM of potassium ferricyanide was dropped onto the CMC layer 7a and dried to form a layer 7b. A glucose sensor was fabricated in such a manner.

Next, as a sample solution, blood conditioned to have a glucose concentration of 30 to 620 mg/dl was prepared. Then, this sample solution was dropped onto the reaction layer 7. When the sample solution containing glucose is supplied to the reaction layer, glucose in the sample is oxidized by the PQQ-GDH. Then, at the same time as the oxidation, potassium ferricyanide in the reaction layer is reduced to potassium ferrocyanide. Here, 30 seconds after the dropping of the sample solution, a voltage of +0.5 V was applied to the working electrode 4 on the basis of the counter electrode 5 so as to oxidize potassium ferrocyanide. Then, 5 seconds later, the value of a current flowing across the counter electrode and the working electrode was measured.

The current value was measured for blood conditioned for a variety of glucose concentrations, and the response characteristic graph of the sensor was produced by plotting the glucose concentration in the horizontal axis and the current value in the vertical axis. The results are shown by the solid line in FIG. 3.

A biosensor fabricated in the same manner was placed in a sealed container containing silica gel as a moisture absorbent and stored for one week at 40° C., and then the response characteristic graph of this biosensor was produced. The results are shown by the dotted line in FIG. 3.

Figure 3:
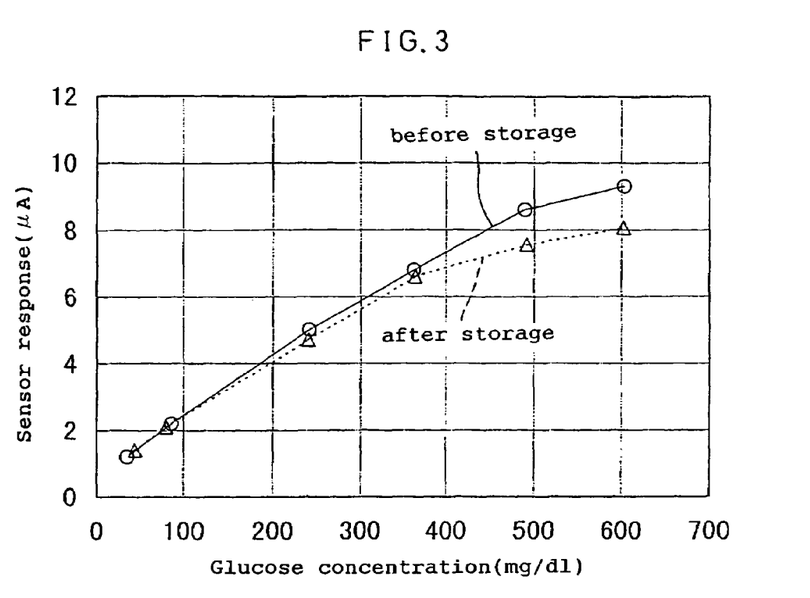
FIG. 3 is a graph showing the response characteristics of a glucose sensor of Comparative Example 1.

It would be understood from FIG. 3 that there is a certain correlation between the glucose concentration and the response current value. However, it would be understood that the response characteristic of the sensor stored for one week at 40° C. was lowered in comparison with the sensor immediately after the fabrication, i.e., before storage.

EXAMPLE 1

After forming the CMC layer 7a in the same manner as in Comparative Example 1, 5 µl of a mixed aqueous solution containing 1000 U/ml of PQQ-GDH, 50 mM of potassium ferricyanide and 40 mM of potassium gluconate was dropped onto the CMC layer 7a and dried to form the layer 7b. A glucose sensor was fabricated in such a manner.

Figure 4:
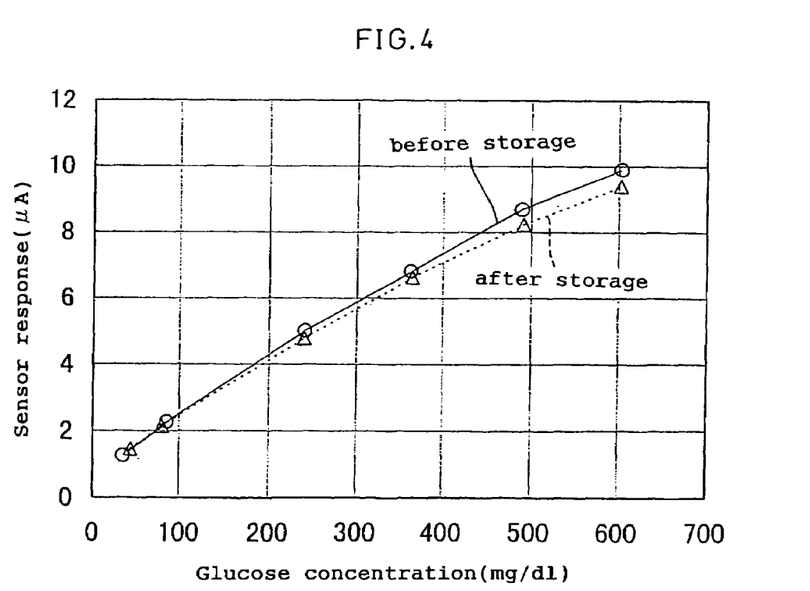
FIG. 4 is a graph showing the response characteristics of a glucose sensor of Example 1 of the present invention.

Next, in the same manner as in Comparative Example 1, the response characteristic graph was produced for the sensor immediately after the fabrication and the sensor after being stored in a sealed container containing silica gel for one week at 40° C. The results are shown in FIG. 4. It would be understood from FIG. 4 that there is a certain correlation between the glucose concentration and the response current value. It would be understood by a comparison with Comparative Example 1 that the sensor of this example had a smaller lowering in the response current value in the response after the one-week storage at 40° C., particularly in a range of not less than 400 mg/dl. Hence, it would be understood that the storage characteristic of the glucose sensor is significantly improved by the addition of potassium gluconate.

Figure 5:
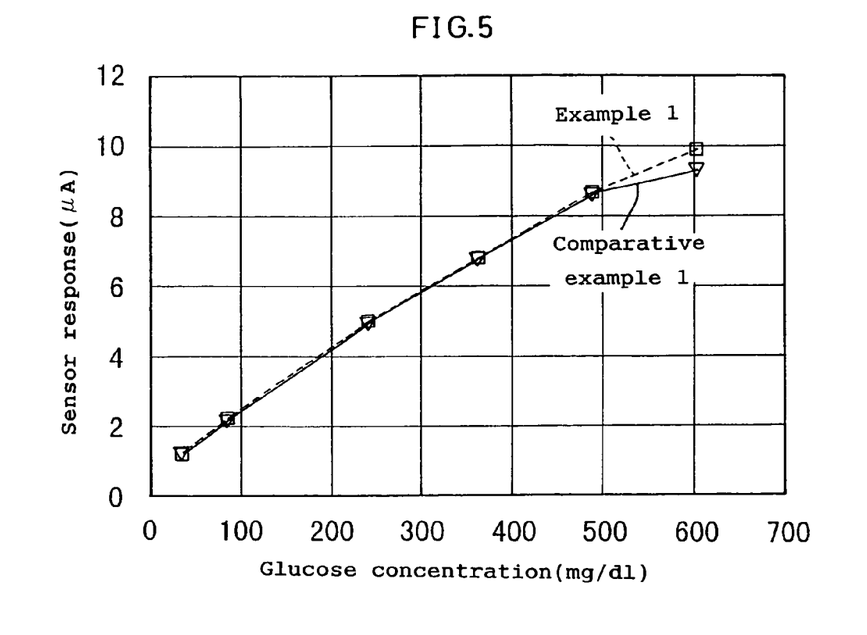
FIG. 5 is a graph showing the response characteristics of the glucose sensor of Example 1 and glucose sensor of Comparative Example 1 before storage.

FIG. 5 shows a comparison of the response characteristics before storage between the sensor of Comparative Example 1 containing no potassium gluconate and the sensor of this example containing potassium gluconate. It is seen from FIG. 5 that the glucose sensor containing potassium gluconate has higher response values in the vicinity of 600 mg/dl than the glucose sensor containing no potassium gluconate. Hence, it would be understood that it is possible to improve the response characteristic of the glucose sensor in a high-concentration range by the addition of potassium gluconate.

EXAMPLE 2

After forming the CMC layer 7a in the same manner as in Comparative Example 1, 5 µl of a mixed aqueous solution containing 1000 U/ml of PQQ-GDH, 50 mM of potassium ferricyanide, 40 mM of potassium gluconate and 0.5 mM of potassium hydrogen phthalate was dropped onto the CMC layer 7a and dried to form the layer 7b. A glucose sensor was fabricated in such a manner.

Figure 6:
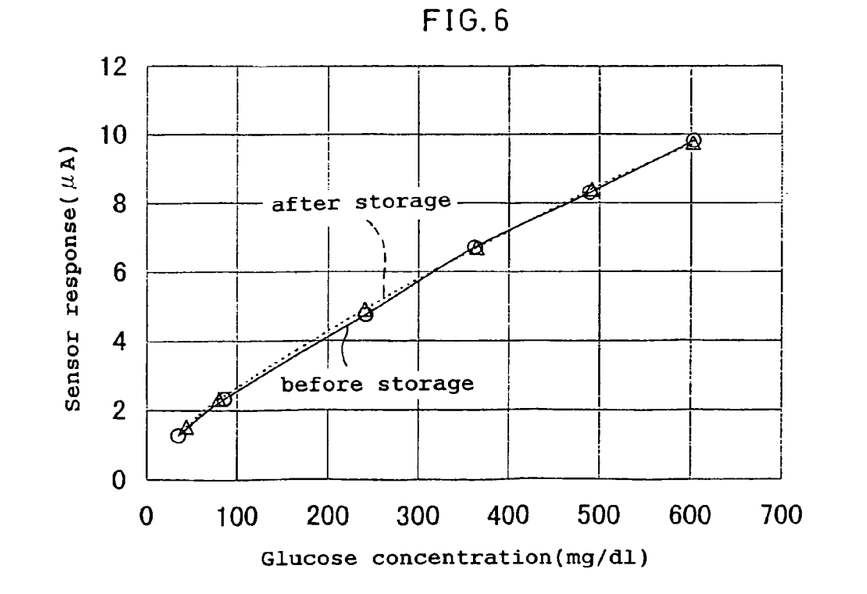
FIG. 6 is a graph showing the response characteristics of a glucose sensor of Example 2 of the present invention.

In the same manner as in Comparative Example 1, the response characteristic graph was produced for the sensor immediately after the fabrication and the sensor after being stored in a sealed container containing silica gel for one week at 40° C. The results are shown in FIG. 6. It would be understood from FIG. 6 that there is almost no difference in the response characteristics between the sensor immediately after the fabrication and the sensor after the one week storage at 40° C., and the storage characteristic of the sensor of this example is significantly improved in comparison with Comparative Example 1.

Figure 7:
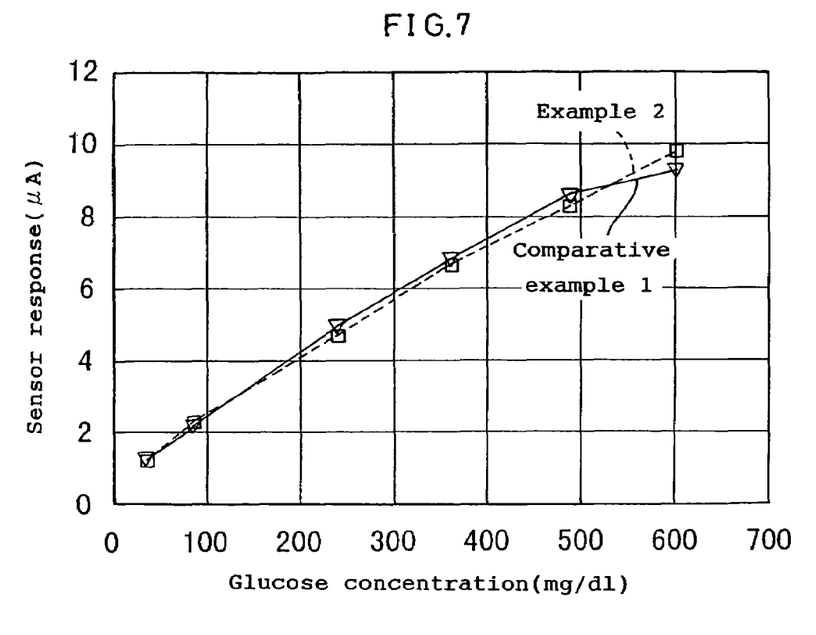
FIG. 7 is a graph showing the response characteristics of the glucose sensor of Example 2 and glucose sensor of Comparative Example 1 before storage.

FIG. 7 shows a comparison of the response characteristics before storage between the sensor of Comparative Example 1 containing no potassium gluconate and the sensor of this example containing potassium gluconate and potassium hydrogen phthalate. It is seen from FIG. 7 that the glucose sensor containing potassium gluconate and potassium hydrogen phthalate has higher response values in the vicinity of 600 mg/dl compared with the glucose sensor of Comparative Example 1. Hence, it would be understood that it is possible to improve the response characteristic of the glucose sensor in a high-concentration range by the addition of potassium gluconate and potassium hydrogen phthalate.

EXAMPLE 3

After forming the CMC layer 7a in the same manner as in Comparative Example 1, 5 µl of a mixed aqueous solution containing 1000 U/ml of PQQ-GDH, 50 mM of potassium ferricyanide, 40 mM of potassium gluconate and 0.5 mM of maleic acid was dropped onto the CMC layer 7a and dried to form the layer 7b. A glucose sensor was fabricated in such a manner.

Figure 8:
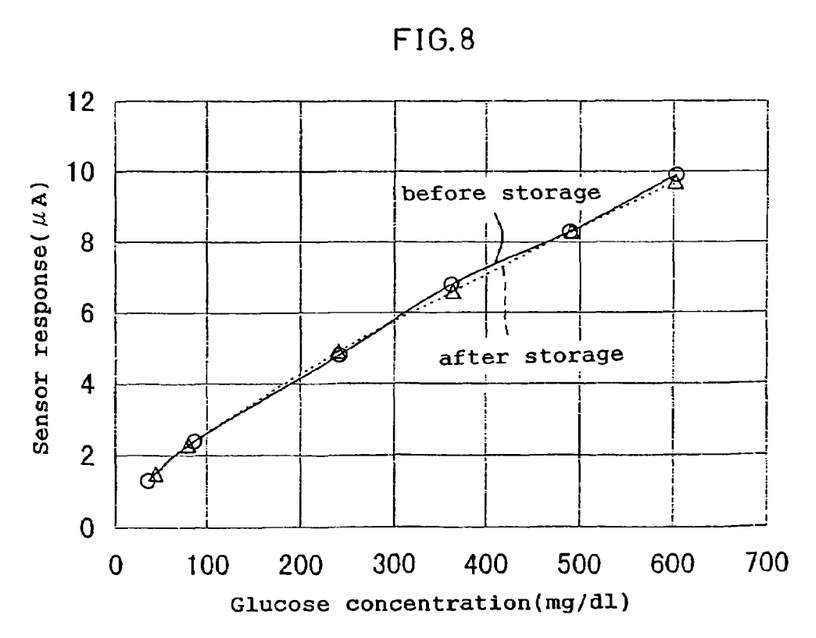
FIG. 8 is a graph showing the response characteristics of a glucose sensor of Example 3 of the present invention.

In the same manner as in Comparative Example 1, the response characteristic graph was produced for the sensor immediately after the fabrication and the sensor after being stored in a sealed container containing silica gel for one week at 40° C. The results are shown in FIG. 8. It would be understood from FIG. 8 that there is almost no difference in the response characteristics between the sensor immediately after the fabrication and the sensor after the one-week storage at 40° C., and the storage characteristic of the sensor of this example is improved in comparison with Comparative Example 1.

Figure 9:
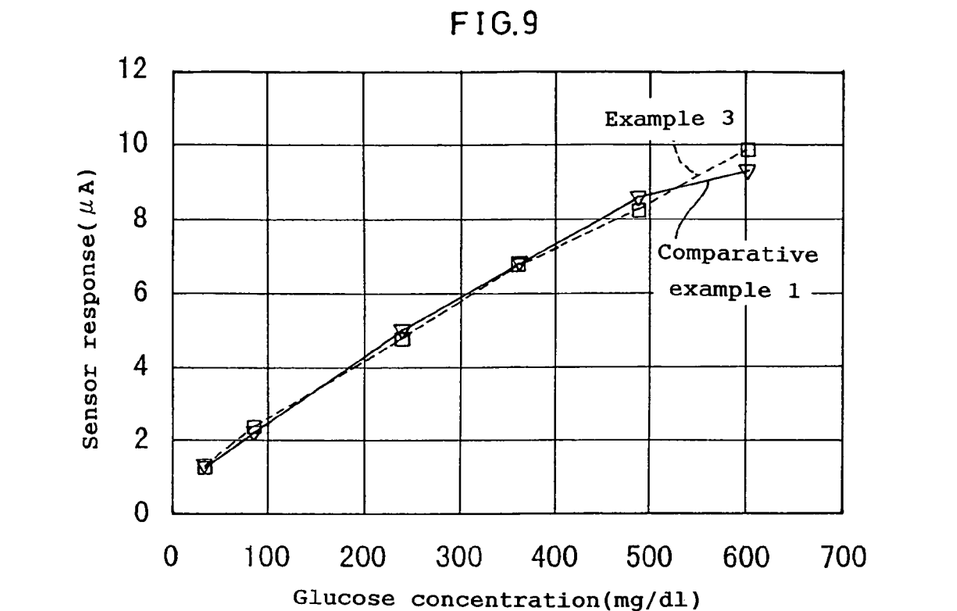
FIG. 9 is a graph showing the response characteristics of the glucose sensor of Example 3 and glucose sensor of Comparative Example 1 before storage.

FIG. 9 shows a comparison of the response characteristics before storage between the sensor of Comparative Example 1 containing no potassium gluconate and the sensor of this example containing potassium gluconate and maleic acid. It is seen from FIG. 9 that the glucose sensor containing potassium gluconate and maleic acid has higher response values in the vicinity of 600 mg/dl. Hence, it would be understood that it is possible to improve the response characteristic of the glucose sensor in a high-concentration range by the addition of potassium gluconate and maleic acid.

EXAMPLE 4

After forming the CMC layer 7a in the same manner as in Comparative Example 1, 5 µl of a mixed aqueous solution containing 1000 U/ml of PQQ-GDH, 50 mM of potassium ferricyanide, 40 mM of potassium gluconate and 0.5 mM of succinic acid was dropped onto the CMC layer 7a and dried to form the layer 7b. A glucose sensor was fabricated in such a manner.

Figure 10:
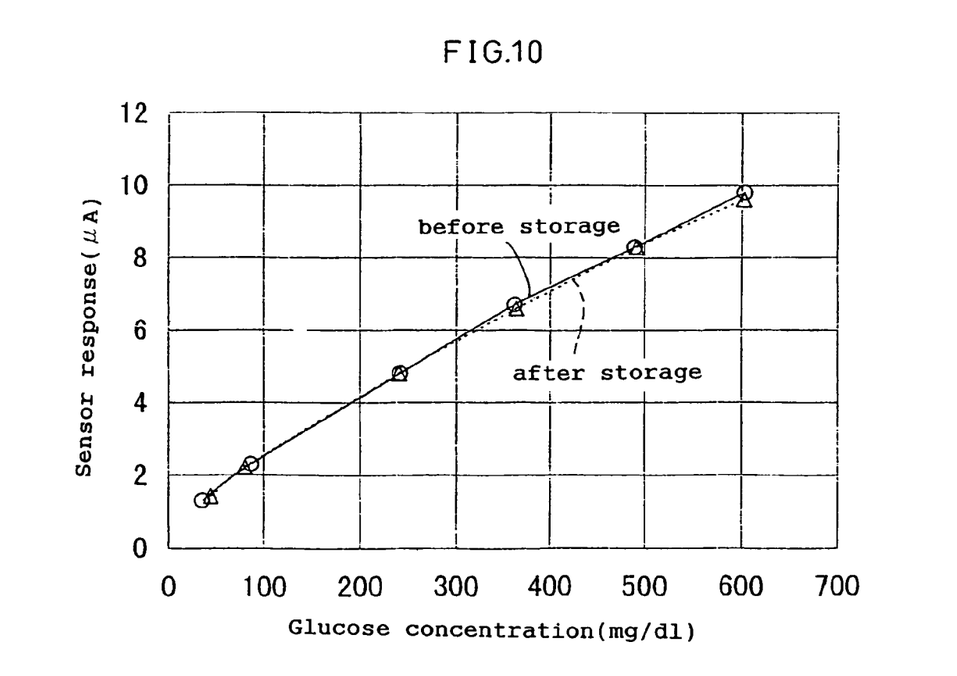
FIG. 10 is a graph showing the response characteristics of a glucose sensor of Example 4 of the present invention.

In the same manner as in Comparative Example 1, the response characteristic graph was produced for the sensor immediately after the fabrication and the sensor after being stored in a sealed container containing silica gel for one week at 40° C. The results are shown in FIG. 10. It would be understood from FIG. 10 that there is almost no difference in the response characteristics between the sensor immediately after the fabrication and the sensor after the one-week storage at 40° C., and the storage characteristic of the sensor of this example is improved in comparison with Comparative Example 1.

Figure 11:
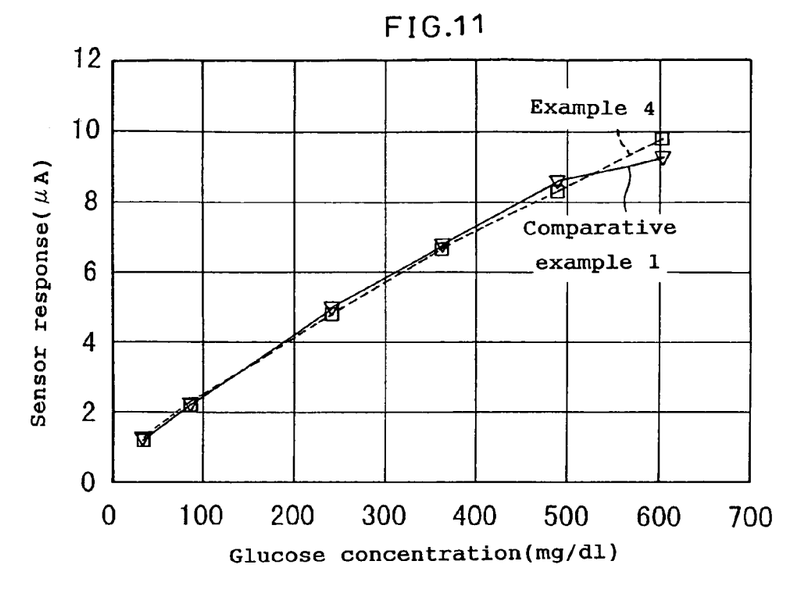
FIG. 11 is a graph showing the response characteristics of the glucose sensor of Example 4 and glucose sensor of Comparative Example 1 before storage.

FIG. 11 shows a comparison of the response characteristics before storage between the sensor of Comparative Example 1 and the sensor of this example containing potassium gluconate and succinic acid. It is seen from FIG. 11 that the glucose sensor containing potassium gluconate and succinic acid has higher response values in the vicinity of 600 mg/dl. Hence, it would be understood that it is possible to improve the response characteristic of the glucose sensor in a high-concentration range by the addition of potassium gluconate and succinic acid.

EXAMPLE 5

After forming the CMC layer 7a in the same manner as in Comparative Example 1, 5 μl of a mixed aqueous solution containing 1000 U/ml of PQQ-GDH, 50 mM of potassium ferricyanide, 40 mM of potassium gluconate, 0.5 mM of potassium hydrogen phthalate and 75 μM of calcium chloride was dropped onto the CMC layer 7a and dried to form the layer 7b. A glucose sensor was fabricated in such a manner.

Figure 12:
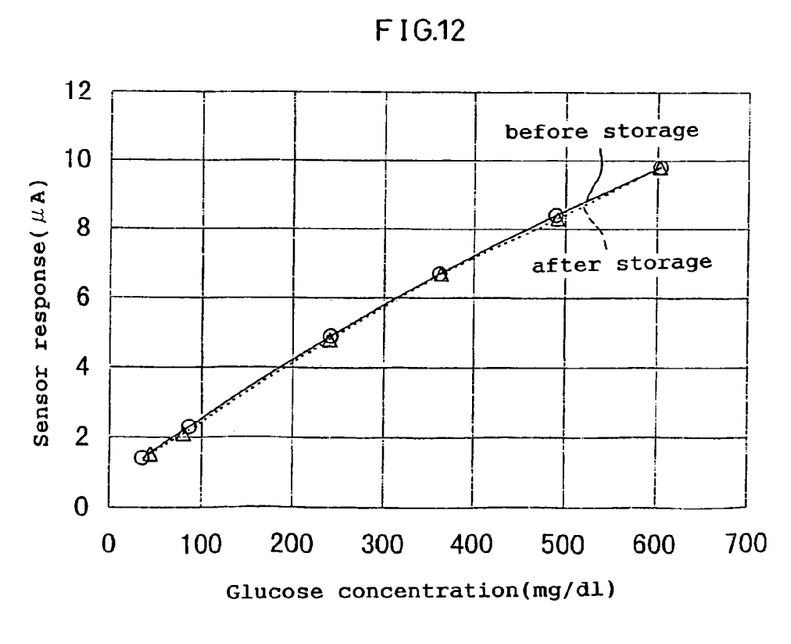
FIG. 12 is a graph showing the response characteristics of a glucose sensor of Example 5 of the present invention.

In the same manner as in Comparative Example 1, the response characteristic graph was produced for the sensor immediately after the fabrication and the sensor after being stored in a sealed container containing silica gel for one week at 40° C. The results are shown in FIG. 12. It would be understood from FIG. 12 that there is almost no difference in the response characteristics between the sensor immediately after the fabrication and the sensor after the one-week storage at 45° C., and the storage characteristic of the sensor of this example is superior under a high-temperature storage condition, that is, one-week storage at 45° C.

INDUSTRIAL APPLICABILITY

According to the present invention, as described above, it is possible to obtain a high-performance glucose sensor having excellent storage stability and an improved response characteristic.

What is claimed is:

1. A glucose sensor comprising: an electrically insulating base plate; an electrode system including at least a working electrode and a counter electrode formed on said base plate; and a reaction layer formed in contact with or in the vicinity of said electrode system, wherein said reaction layer contains an admixture of at least pyrrolo-quinoline quinone dependent glucose dehydrogenase and potassium gluconate and wherein the glucose sensor is in a sealed container.

2. The glucose sensor as set forth in claim 1, wherein said reaction layer further contains at least one additive selected from the group consisting of phthalic acid, salts of phthalic acid, maleic acid, salts of maleic acid, succinic acid and salts of succinic acid.

3. The glucose sensor as set forth in claim 2, wherein said reaction layer further contains calcium ions.

4. The glucose sensor as set forth in claim 2, wherein said reaction layer further contains an electron mediator.

5. The glucose sensor as set forth in claim 1, wherein said reaction layer further contains calcium ions.

6. The glucose sensor as set forth in claim 5, wherein said reaction layer further contains an electron mediator.

7. The glucose sensor as set forth in claim 1, wherein said reaction layer further contains an electron mediator.

8. The glucose sensor as set forth in claim 1, wherein said reaction layer further contains an electron mediator.

9. The glucose sensor as set forth in claim 1 wherein the amount of potassium gluconate is within the range of 1.5 to 150 μg and the amount of glucose dehydrogenase is 0.2 to 20 U.

10. A glucose sensor comprising: an electrically insulating base plate; an electrode system including at least a working electrode and a counter electrode formed on said base plate; and a reaction layer formed in contact with or in the vicinity of said electrode system, wherein said reaction layer contains an admixture of at least pyrrolo-quinoline quinone dependent glucose dehydrogenase and potassium gluconate, wherein the response of the sensor immediately fabricated is substantially the same as compared to the sensor after being stored for one week at 40° C.

11. The glucose sensor as set forth in claim 10 in a sealed container.

12. The glucose sensor as set forth in claim 10 wherein the amount of potassium gluconate is within the range of 1.5 to 150 μg and the amount of glucose dehydrogenase is 0.2 to 20 U.

13. A glucose sensor comprising: an electrically insulating base plate; an electrode system including at least a working electrode and a counter electrode formed on said base plate; and a reaction layer containing at least pyrrolo-quinoline quinone dependent glucose dehydrogenase, formed in contact with or in the vicinity of said electrode system, wherein said reaction layer contains potassium gluconate and one additive selected from the group consisting of phthalic acid, salts of phthalic acid, maleic acid, salts of maleic acid, succinic acid and salts of succinic acid.

* * * * *

UNITED STATES PATENT AND TRADEMARK OFFICE
CERTIFICATE OF CORRECTION

| | | |
|---|---|---|
| PATENT NO. | : 7,005,048 B1 | Page 1 of 1 |
| APPLICATION NO. | : 09/807692 | |
| DATED | : February 28, 2006 | |
| INVENTOR(S) | : Motokazu Watanabe et al. | |

It is certified that error appears in the above-identified patent and that said Letters Patent is hereby corrected as shown below:

On the Title page of the Letters Patent,

Under section "(56) Reference Cited, OTHER PUBLICATIONS", insert omitted reference -- CAPLUS MASLINSKA-SOLICH", Maleic Anhydride Copolymers in Clinical Analysis" Chemia Stosowana (1990), 34 (1-2, 11-22) --

Signed and Sealed this

Twelfth Day of December, 2006

JON W. DUDAS
*Director of the United States Patent and Trademark Office*